United States Patent [19]

Reynolds et al.

[11] Patent Number: 5,325,851
[45] Date of Patent: Jul. 5, 1994

[54] APPARATUS AND METHOD FOR VENTILATING AND ASPIRATING

[75] Inventors: Valdon G. Reynolds; Gordon S. Reynolds, both of Bountiful; Joseph T. Sorenson, Murray, all of Utah

[73] Assignee: Sorenson Laboratories, Inc., Salt Lake City, Utah

[21] Appl. No.: 678,663

[22] Filed: Apr. 1, 1991

[51] Int. Cl.$^5$ .............................................. A61M 16/00
[52] U.S. Cl. ........................... 128/207.16; 128/207.14
[58] Field of Search ..................... 128/200.26, 207.14, 128/207.15, 207.16

[56] References Cited

U.S. PATENT DOCUMENTS

| | | | |
|---|---|---|---|
| 1,120,549 | 12/1914 | Schellberg | 604/171 |
| 3,517,669 | 3/1968 | Buono et al. | 604/119 |
| 3,628,532 | 12/1971 | Magrath | 128/207.16 |
| 3,730,179 | 5/1973 | Williams | 128/204.18 |
| 3,757,771 | 9/1973 | Ruegg et al. | 604/163 |
| 3,991,762 | 11/1976 | Radford | 128/207.16 |
| 4,036,210 | 7/1977 | Campbell et al. | 128/207.16 |
| 4,193,406 | 3/1980 | Jinotti | 128/204.18 |
| 4,212,300 | 7/1980 | Meals | 604/119 |
| 4,300,550 | 11/1981 | Gandi et al. | 128/207.18 |
| 4,327,723 | 5/1982 | Frankhouser | 604/171 |
| 4,451,257 | 5/1984 | Atchley | 604/119 |
| 4,595,005 | 6/1986 | Jinotti | 128/205.24 |
| 4,638,539 | 1/1987 | Palmer | 128/207.16 |
| 4,696,296 | 9/1987 | Palmer | 128/207.16 |
| 4,805,611 | 2/1989 | Hodgkins | 604/171 |
| 4,834,726 | 5/1989 | Lumbert | 604/281 |
| 4,836,199 | 6/1989 | Palmer | 128/207.16 |
| 4,872,579 | 10/1989 | Palmer | 128/207.16 |
| 4,938,741 | 7/1990 | Lumbert | 604/19 |
| 4,981,466 | 1/1991 | Lumbert | 604/19 |
| 5,029,580 | 7/1991 | Radford et al. | 604/43 |
| 5,073,164 | 12/1991 | Hollister et al. | 604/43 |
| 5,083,561 | 1/1992 | Russo | 128/207.16 |
| 5,134,996 | 8/1992 | Bell | 604/163 |

Primary Examiner—Edgar S. Burr
Assistant Examiner—Aaron J. Lewis
Attorney, Agent, or Firm—Trask, Britt & Rossa

[57] ABSTRACT

A ventilating and aspirating apparatus for delivering respiratory gases to the trachea of a patient and aspirating congested lungs and breathing passageways includes a flexible catheter tube extendable into and withdrawable from the patient's trachea, a resilient pliable sheath lending a structural rigidity to the apparatus and receiving the catheter tube when withdrawn from the patient, a valve structure attached to the catheter tube which is slidable along the length of the sheath, a manifold structure and swivel mounting means to allow coaxial swivel motion of the components, and a collapsible/extendable sealing envelope structure arranged to cover components on the proximal side of the manifold.

38 Claims, 4 Drawing Sheets

APPARATUS AND METHOD FOR VENTILATING AND ASPIRATING

BACKGROUND OF THE INVENTION

1. Field

This invention relates generally to an apparatus for ventilating and aspirating the lungs of a medical patient and is particularly directed to an improved apparatus and method for ventilating and aspirating congested lungs and obstructed breathing passageways.

2. State Of the Art

Several issued U.S. patents disclose ventilating and aspirating apparatus. Notable among these patents are U.S. Pat. Nos. 4,836,199; 4,569,344; and 3,991,762, each of which discloses a device in which a flexible catheter tube is sealed inside a collapsible plastic envelope. This arrangement is intended to assure sterility even when the catheter tube is removed from the trachea of a patient. The catheter of the device is attached at its proximal (user) end to a valve so that a vacuum source can be selectively communicated to the catheter lumen. The device also contains a manifold which attaches to a endotracheal tube and a ventilating fixture. Insertion of the catheter tube into the trachea of a patient is accomplished by grasping the catheter tube through the envelope and manually moving it into the trachea. Each of these devices also contains a port through which the exterior of the catheter tube can be rinsed with a suitable irrigating solution. The '762 patent further discloses a wheel attached to the catheter tube so that it can be rotated during its insertion or removal.

Several disadvantages exist with respect to this class of ventilating/aspirating devices. The catheter tubes are relatively pliant and lack any structural reinforcement. Accordingly, the device tends to fall where it may, interfering with both patient movement and patient care. Further, the device itself tends to interfere with other structures attached to the patient. Structures such as intravenous delivery tubing or electronic sensors may become tangled with the pliant catheter tube. Moreover, the catheter tube cannot conveniently be taped to the patient or secured out of the way because it must be positioned generally in line with an endotracheal tube to facilitate insertion of the catheter into the patient.

These devices also require a user to employ both hands when inserting the catheter into the trachea of a patient. One hand must grasp the catheter tube to insert it incrementally into the trachea, while the other hand must hold either the manifold body (to ease insertion) or the proximal end of the device (to keep it out of the way). If aspiration is desired during the insertion step, a second person must operate the valve.

Indiscriminate movement of the pliant catheter tube, repeated insertions into the patient, or exposure to objects which can penetrate the flexible envelope result in inadequate assurance of sterility. Pin holes in the envelope can easily occur, exposing the catheter to outside air and destroying sterility of the catheter.

U.S. Pat. Nos. 4,938,741 and 4,981,466 disclose a suctioning catheter tube with an elbow bend at the distal (patient) end. The purpose of the bend is to facilitate entry of the catheter into the left bronchus. The left bronchus is disposed at an angle from the trachea making it more difficult to enter than the right bronchus. The elbow bend, however, is temporary. A retaining device must be inserted into the distal end of the catheter tube to retain the bend during storage. The bend must be heated before use to destroy the memory of the linear catheter tube and set the bend.

It is known to provide a radiopaque band at the distal end of a catheter to aid in placement of the catheter in either bronchus. The radiopaque band reveals the linear positioning of the distal end of the catheter but is incapable of relaying information concerning the direction in which the distal end beyond an elbow is pointing. Proper orientation of the distal end is helpful for proper placement of the catheter in a bronchus. To obtain positioning information via radiopaque bands requires expensive radiological equipment to locate the band during catheter insertion. Such equipment is not always available as, for example, to a paramedic at an accident scene. In instances in which locating the radio indicia on the catheter would be the only purpose for radiological services, such services cannot ordinarily be economically justified to the patient.

SUMMARY OF THE INVENTION

The present invention provides both an improved apparatus and an improved method for simultaneously ventilating and aspirating a medical patient. The invention enables a user to insert a flexible catheter tube into either lung of a patient in one smooth motion without risk of contamination or infection. Additionally, a user is able to activate, in one motion, a vacuum valve to evacuate undesired respiratory fluids and simultaneously ventilate and/or irrigate the lungs.

A flexible catheter tube is attached at the proximal (user) end to a valve. The valve is selectively actuated to communicate a vacuum suction to the lumen of the catheter. The distal (patient) end of the catheter tube is structured to permit fluids to be suctioned into the lumen of the catheter tube. The distal end may also include an elbow bend orienting the distal end of the catheter tube at any desired angle but ideally at approximately 20 degrees. The elbow bend is located near, typically approximately one inch from, the distal tip of the catheter tube. The distal end of the catheter tube is thereby inclined from the central longitudinal axis of the catheter tube to facilitate entry of the catheter tube into the patient's bronchi, especially the left bronchus.

The vacuum valve at the proximal end of the catheter tube is used to communicate a suctioning vacuum to the lumen of the catheter. A typical such suctioning vacuum source is the vacuum line in a hospital room. The valve contains a biasing means which urges the valve to a normally closed position. This structure is also a component of a valve actuator. Ideally, the biasing means of the valve is structured as a resilient cap carrying a depending valve stem. The stem is arranged for mounting in a valve body having an inlet and an outlet. When a suctioning vacuum is desired, the user presses the biasing means, thereby actuating the valve stem, bringing the catheter into fluid flow communication with the vacuum source. This simple vacuum valve arrangement obviates the need for a user to involve more than one hand either to actuate the valve or to lock it in an open position. The user's other hand is thereby left free to aid in placement or movement of the catheter. The valve is protected against inadvertent actuation by a shield element surrounding the valve actuator. The entire valve assembly serves as a convenient handle for inserting and withdrawing the catheter tube.

The catheter tube is slidable lengthwise through a multi-function manifold positioned at the distal end of the apparatus. The manifold consists of several segments and includes a port at the distal end for communication with an endotracheal tube inserted into the patient. The distal port is positioned at the end of a generally cylindrical passageway which extends through the length of the manifold. A proximal port is located at the opposite end of the passageway. The catheter tube is slidable through this passageway so that it enters the endotracheal tube through the distal port. A ventilating structure extends radially from the passageway and is in fluid communication with the interior of the passageway. Ambient air, oxygenated air, and other therapeutic gases can be selectively introduced into the respiratory system of the patient through the ventilating structure. The ventilating structure may be formed so that ventilation can be accomplished by inhalation and exhalation of ventilating air through the same conduit or, in an alternate configuration, through two or more conduits, allowing inhalation of ambient air through one port and exhalation through a second port. A third conduit may also be provided for the introduction of other suitable gases to the respiratory system.

The manifold may be disposed between front (distal) and rear (proximal) swivel segments which allow the manifold to rotate in a generally coaxial manner about the catheter tube. The apparatus and any connected devices may thus be moved about independent of the endotracheal tube inserted into the patient. As a consequence, the accessibility of conduits associated with the manifold is enhanced. The attachment of tubing such as the ventilation source is thereby facilitated. A user may rotate the catheter as convenient to perform the aspiration function. Moreover, orientation of the elbow bend for insertion into a bronchus is facilitated.

The rear swivel segment is adapted to receive in its interior a silicone seal or "O"-ring which fits snugly over the catheter tube. A seal is thereby effected between the outside wall of the catheter tube and the inside wall of the "O"-ring. The distal portion of the catheter tube extending beyond the seal is thereby isolated. The seal is snug enough to be air tight but loose fitting enough to allow both linear movement of the catheter tube through the "O"-ring and rotational movement of the swivel coaxially about the catheter tube. The rear swivel segment also contains an irrigation port terminating a conduit disposed at an angle to direct injected irrigating solution onto the catheter tube and toward the patient. Suitable irrigating solutions can be introduced through the irrigation port while the catheter tube is in the advanced position in the trachea or bronchi of the patient. The irrigating solutions flow down the external surface of the catheter tube and into the lungs of the patient providing antimicrobial activity and loosening and diluting phlegm and other undesired respiratory fluids. Fluids may then be aspirated out of the lungs through the catheter tube.

Irrigating solutions may also be introduced as the previously inserted catheter tube is withdrawn from the respiratory tract. Disinfecting and rinsing activity is thereby provided on the external surface of the catheter tube. The swivel connections allow the complete perimeter of the catheter to be rinsed with the irrigating solution. Excess fluid may be evacuated during withdrawal of the catheter.

A semirigid sheath entirely surrounds the catheter tube when the tube is withdrawn from the patient. This sheath is fastened at its distal end to the manifold and thus is in effect an extension of the cylindrical passageway through the manifold. The proximal end of the sheath is closed by a cap which seals the interior from contamination. The sheath is preferably split parallel its central axis, longitudinally substantially along its entire length, providing a pathway for structure connecting the catheter to the valve.

The semirigid sheath performs several important functions. The structural reinforcement provided by the sheath enables a user to insert the catheter into the patient in one smooth motion. This advantage is due to the catheter tube being properly positioned for insertion while the device is attached to the endotracheal tube. When the catheter tube is being inserted, the sheath acts as a guide to direct the tube through the manifold, thereby eliminating kinking and collapsing of the tube and correspondingly, the need for incremental insertion. The sheath also ensures that the device remains in a predictable and stable position when attached to the patient's endotracheal tube, thereby avoiding interference with other tubing and electrical wires which may also be attached to the patient. Finally, the sheath provides an added measure of assurance of sterility while the catheter is withdrawn from the patient.

The term "semirigid," as used in this disclosure, refers to structures such as plastic conduits which are both pliable and resilient. Thick walled, medical grade plastic tubing constitutes a suitable construction material for a semirigid sheath of this invention.

A notable feature of the preferred embodiments of this invention is the relationship between the vacuum valve, the longitudinal split in the semirigid sheath, and the catheter tube. The valve actuating structure is positioned outside the sheath for convenient operation by the user. The longitudinal split in the sheath allows a slider portion of the valve to extend through the split into the interior of the sheath for attachment to the catheter tube. This relationship allows the slider portion of the valve to move longitudinally through the split to effect an insertion or withdrawal of the catheter tube. A resilient sheath provides a gripping effect by the opposed split surfaces of the sheath against the slider portion. This gripping, combined with the snug fit of the "O"-ring against the catheter tube, permits the catheter tube to be positively positioned anywhere along the patient's trachea or bronchi.

The precise position of the valve with respect to the elbow bend at the distal end of the catheter tube constitutes an important feature of certain embodiments of the invention. An indicia may be associated with the valve to indicate the direction that the distal end beyond the bend is pointed. When the catheter tube is being inserted, the user can determine the orientation of the distal end by reference to the valve.

A collapsible plastic envelope surrounds the semirigid sheath and seals it from contamination and contact by the user. The collapsible sheath may be separated into two pieces, one connected between the manifold and the distal side of the valve, the other connected between the proximal side of the valve and the cap at the proximal end of the apparatus.

BRIEF DESCRIPTION OF THE DRAWINGS

In the drawings, which illustrate what is currently regarded as the best mode for carrying out the invention:

FIG. 3b is a view in end elevation of some of the components shown by FIG. 3a.

DETAILED DESCRIPTION OF THE ILLUSTRATED EMBODIMENT

Figure 1:
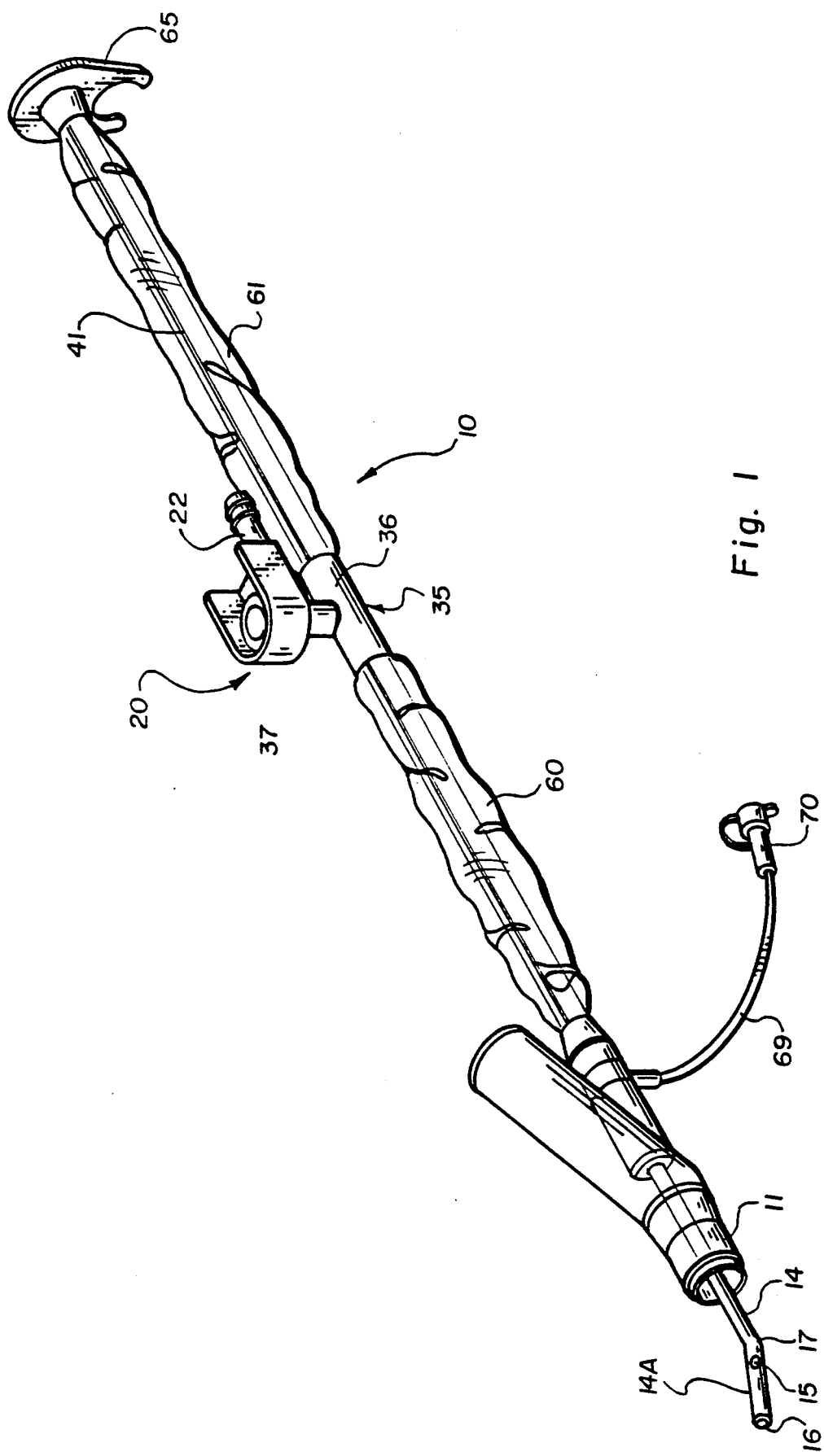
FIG. 1 is a perspective view of a preferred embodiment of the assembled invention.

The ventilating and aspirating device, designated generally 10, includes front swivel segment 11 which attaches to an endotracheal tube, a fragment which is indicated generally 13, associated with a patient (not shown).

A suction catheter tube 14 includes a distal (patient) end 14A and a proximal end 14B. The distal end 14A includes radially disposed perforations 15 and an open end 16. An elbow bend 17 is disposed near the distal end 14A as shown. The proximal end 14B of the catheter tube 14 is attached to a valve denoted generally 20. During operation, the valve 20 is attached to a vacuum source (not shown) by means of vacuum conduit 22. The valve 20 is actuated to apply suction to the lumen of the catheter tube 14.

When the catheter tube 14 is inserted into the endotracheal tube 13 of the patient, the distal end 14A moves into either the endotracheal tube or a bronchus of the patient, depending on the depth of insertion. The elbow bend 17 facilitates entry of the catheter tube 14 into the patient's bronchi. The elbow bend 17 is especially useful in entering the patient's left bronchus which is disposed from the trachea at a more severe angle than is the right bronchus. Undesired respiratory fluids can be suctioned out of the patient's breathing passageways by actuating the valve 20. With vacuum communicated to the catheter tube 14, fluids and secretions are suctioned into the catheter tube lumen through the perforations 15 and open end 16. The fluids and secretions are then transferred out through conduit 22 of the valve 20.

Figure 2:
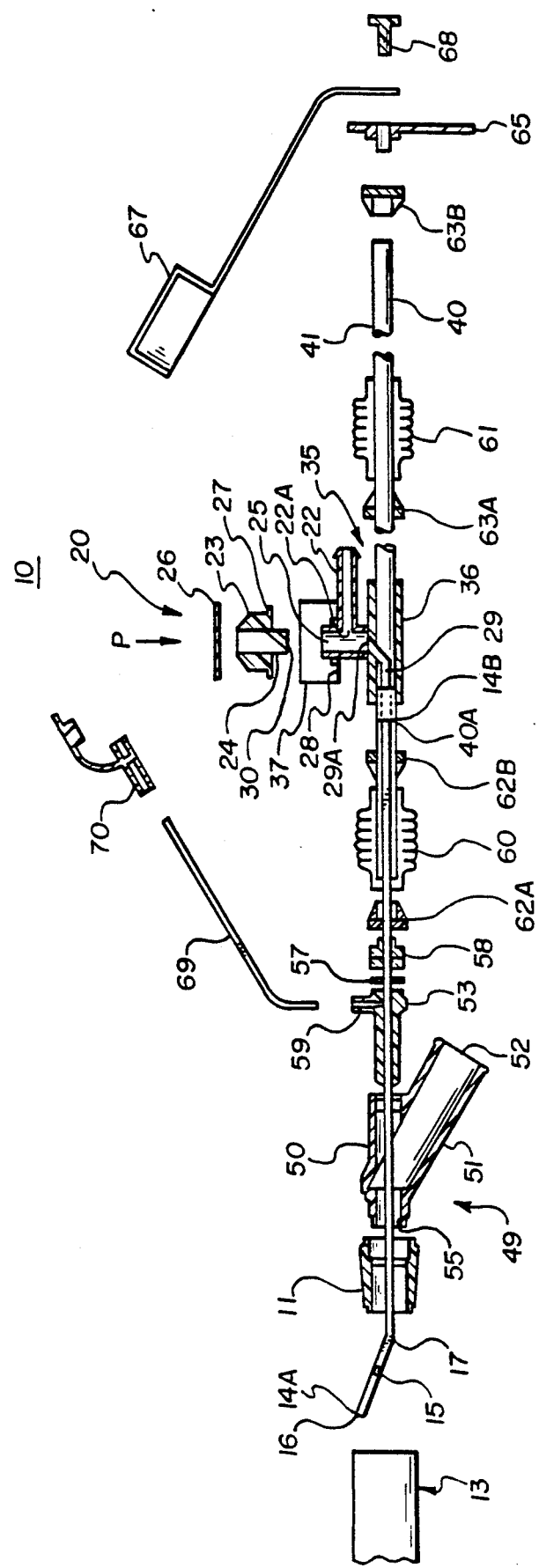
FIG. 2 is an exploded view of the embodiment of FIG. 1.
Figure 3A:
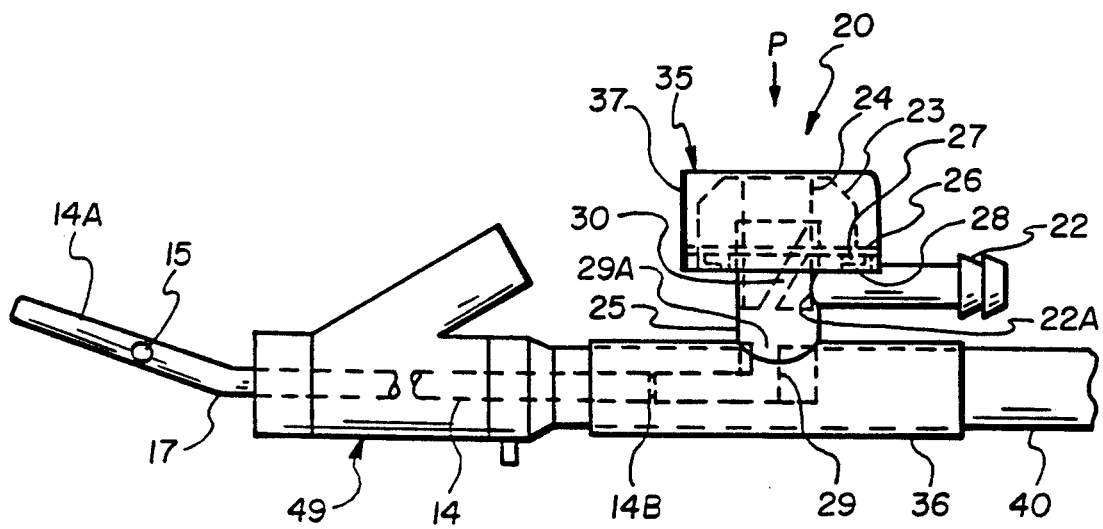
FIG. 3a is an enlarged view in side elevation of certain components shown in FIG. 2.

As best shown by FIGS. 2 and 3a, the valve 20 includes a resilient cap 23 which suspends a depending valve stem 24 in a close-fit relation with a cylindrical valve body 25. When the valve 20 is assembled, a retaining ring 26 locks a skirt 27 of the cap 23 into an annular channel 28 to enclose the valve body 25. With vacuum applied to the conduit 22 the flexible stem 24 is drawn into a sealing relation with port 22A defined by the conduit 22. When the cap 23 is pressed in the direction indicated P, an internal channel 30 of the stem 24 is brought into alignment with the port 22A and the port 29A defined by an inlet conduit 29 depending from the valve body 25. Vacuum is then applied to the lumen of the catheter tube 14. When finger pressure P is released, the resilience of the cap 23 biases the stem 24 upward to the normally closed condition of the valve 20 with the stem 24 again sealing the port 22A.

The valve 20 is associated with a slider assembly 35, which includes, in addition to the valve components enumerated, a slider cylinder 36 and a protective housing 37. The protective housing 37 encloses the valve body 25 and the resilient cap 23 such that skirt 27 is enclosed by and seals against the internal surfaces of the protective housing 37. The protective housing 37 guards against inadvertent actuation of the valve 20.

Referring to FIGS. 1 and 2, a semirigid sheath 40 receives and coaxially surrounds the catheter tube 14 when it is withdrawn from a patient. The sheath 40 has a longitudinal split 41 (FIG. 1) which extends substantially the entire length of the sheath 40. The cylinder 36 of the slider assembly 35 fits coaxially over the semirigid sheath 40. The inlet conduit 29 extends through the longitudinal split 41 into the interior of the sheath 40 where it attaches to the proximal end 14B of catheter tube 14. This arrangement of the valve slider assembly 35 and semirigid sheath 40 enables the valve 20 to be placed outside the sheath 40 where it is accessible to the user for use as a slider handle. Longitudinal movement of the valve 20 along the semirigid sheath 40 moves the catheter 14 into and out of the sheath 40 as required. The catheter tube 14 can thus be inserted and withdrawn from the patient simply by moving valve 20 toward or away from the patient. The gripping action of the opposing edges of the sheath 40 defining the split 41 restrains the catheter 14 from accidental movement into a patient.

Figure 4:
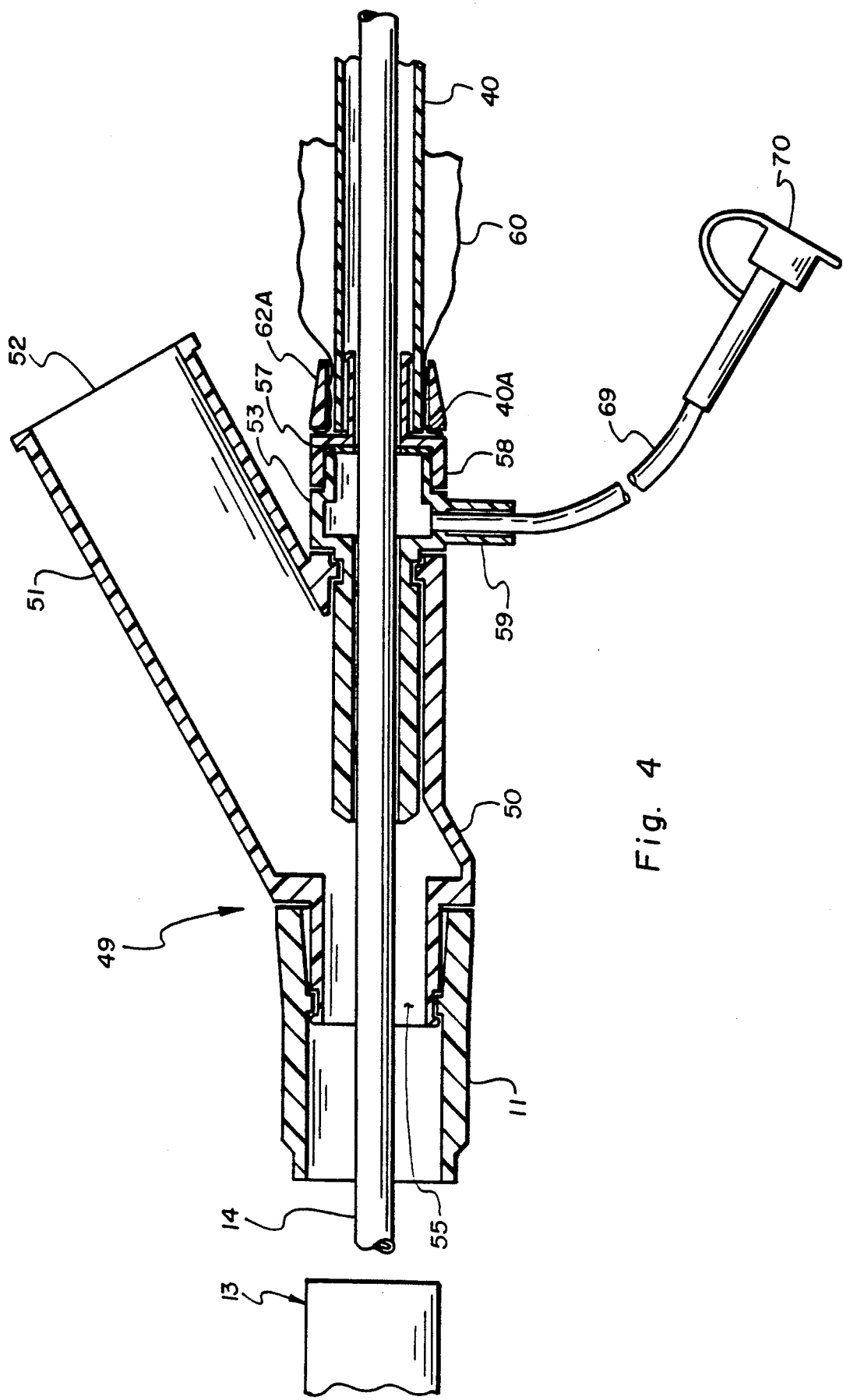
FIG. 4 is an enlarged view of a portion of the embodiment shown in FIG. 2.

Referring to FIG. 4, a segmented manifold assembly denoted generally 49 is indirectly attached to the distal end 40A of the semirigid sheath 40. This assembly 49 includes port casing 50, ventilation conduit 51, and ventilation port 52 disposed between rear swivel segment 53 and front swivel segment 11.

Port casing 50 includes a generally cylindrical passage 55 through which catheter tube 14 moves during insertion or withdrawal. Ventilation conduit 51 extends radially from port casing 50 and is in fluid communication with the interior of the passage 55. Ambient air, oxygenated air, and other therapeutic gases can be selectively introduced into the respiratory system of the patient through ventilation port 52.

The front swivel segment 11 attaches to the port casing 50 at the distal end of the passage 55. The attachment is such that the passage 55 communicates with the interior of the front swivel segment 11. The connection between the front swivel segment 11 and port casing 50 is sufficiently fluid tight to maintain a sterile, air-tight seal but loose fitting enough to allow independent rotation of each segment. The front swivel segment 11 is adapted to attach to the patient's endotracheal tube 13 such that the passage 55 is in fluid communication with the endotracheal tube 13.

The rear swivel segment 53 attaches to the port casing 50 at the proximal end of the passage 55 in a fashion generally similar to that explained in connection with the front swivel segment 11. The passage 55 communicates with the interior of the rear swivel segment 53. The connection effected between the casing 50 and segment 53 also allows independent rotation of the segments as previously described.

Figure 3B:
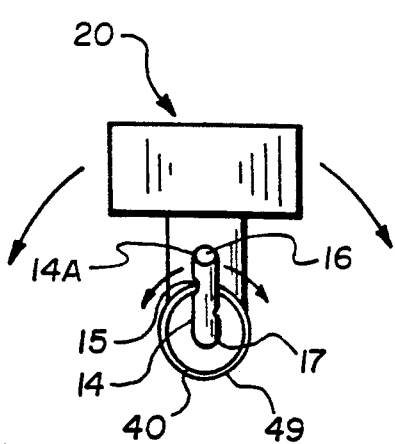

FIG. 3a illustrates the arrangement of the semirigid sheath 40, valve 20, swivel mounted manifold means 49, and catheter tube 14. To aid in inserting the catheter tube 14 into the left bronchus, elbow bend 17 is disposed near the distal end 14A of the catheter tube 14. The elbow bend 17, however, is more helpful if the user knows the orientation of the distal end 14A. The valve 20, being attached to the proximal end 14B of the catheter tube 14, provides a positional index relative to the orientation of distal end 14A. The fixed relationship between the valve 20 and the distal end 14A, as shown in FIG. 3b, coupled with the swivel capability of the manifold 49, allows the user to orient the distal end 14A so that the catheter tube 14 can easily be inserted into the patient's left bronchus. The semirigid sheath 40 ensures that the device is structurally supported so that the positional relationship between the valve 20 and distal end 14A is readily evident to the user.

Referring again to FIG. 4, the rear swivel segment 53 carries an "O"-ring 57 which is held in place by a seal cover 58. The "O"-ring 57 thus fits snugly to form a seal between the inside wall of the segment 53 and the outside wall of the "O"-ring 57. The interior surface of the "O"-ring 57 fits snugly over the catheter tube 14, forming an air-tight sterility seal. The catheter tube 14 is slidable lengthwise through the "O"-ring 57 during insertion or withdrawal of the catheter tube 14 with respect to a patient. The extended portion of the catheter tube 14 is thereby isolated from the remainder of the device 10.

Molded into the exterior wall of the rear swivel segment 53 is an irrigation extension conduit 59 which is in fluid communication with the passage 55. When an irrigating solution is injected into the conduit 59, the solution is directed onto the exterior of the catheter tube 14 and flows down the catheter tube 14 toward its distal end 14A.

The assemblage of the casing segment 50, front swivel segment 11, and rear swivel segment 53 permits each of these segments to rotate coaxially around the catheter tube 14 independent of the other segments. Several significant advantages follow from this arrangement. The accessibility of ventilation conduit 51 during attachment of the ventilation source is enhanced. The casing segment 50 and any attached hoses or tubing can also be swiveled out of the way of the user or the patient during use. The catheter tube 14 may be rotated during use to facilitate aspiration. Moreover, the irrigation conduit 59 can be pivoted to allow rinsing of the complete perimeter of the catheter tube 14 during withdrawal.

A collapsible envelope is provided in two portions, 60 and 61. This envelope surrounds the semirigid sheath 40 and is intended to assure sterility of the device during use. The distal portion 60 of the collapsible sheath attaches between the distal end of the valve 20 and the proximal end of the rear swivel segment 53 by means of locking collars 62A and 62B (FIG. 2). The proximal portion 61 of the collapsible envelope attaches between the proximal end of the valve 20 and the proximal end of the device by means of locking collars 63A and 63B. During insertion of the catheter tube 14 into the patient, the distal portion 60 of the collapsible envelope shortens in length as the valve 20 slides toward the manifold assembly 49 while the proximal portion 61 of the envelope extends as the valve 20 moves away from the proximal end of the device 10. This relationship is reversed during withdrawal of the catheter tube 14 by moving the valve 20 in the opposite direction towards the proximal end of the device 10.

A hose clip 65 facilitates fastening the device 10 out of the way during periods of non-use.

A slider locking cap 67 is shown at the proximal end of the device 10 being held in place by the lock wedge 68. The wedge 68 seals the open end of the split tubing 40 and holds the proximal components 63B, 65, and 67 in place. The locking cap 67 fits over the shield 37 of the sliding valve assembly 20 when properly positioned to hold the catheter tube 14 in its fully retracted position prior to use. It also isolates the valve cap 23 from inadvertent actuation and preserves the cleanliness of the components of the valve assembly 20. Conventional PVC tubing 69 and an end fixture 70 are illustrated in association with the irrigation extension conduit 59.

Reference herein to the details of the illustrated embodiment is by way of example only and is not intended to limit the scope of the appended claims which themselves recite those details regarded as important to the invention.

What is claimed is:

1. A ventilating and aspirating apparatus for delivering respiratory gases to the trachea of a patient and aspirating congested lungs and breathing passageways comprising:

a flexible catheter tube having a catheter lumen and a longitudinal catheter axis, said catheter tube being extendable into and withdrawable from a patient's trachea and having a distal end structured to permit secretions to enter said catheter lumen;

a vacuum valve with an inlet connected to the lumen of said catheter tube, an outlet constituting means for connection to a vacuum source, and an actuator for selectively communicating the lumen of said catheter tube with the vacuum source;

a resilient, pliable sheath having a longitudinal sheath axis, said sheath receiving and coaxially surrounding said catheter tube and having an open distal end through which said catheter tube is slidable;

a manifold connected to the distal end of said sheath and having a center passage in open communication with the interior of said sheath, said manifold including means for establishing a fluid connection between said center passage and a patient ventilation and exhalation apparatus and being structured to permit slidable passage of said catheter tube through said center passage; and an "O"-ring disposed within said manifold, said "O"-ring fitting coaxially over said catheter tube thereby isolating the distal portion of said catheter tube extending beyond said "O"-ring.

2. The ventilating and aspirating apparatus of claim 1 wherein said manifold includes a segment rotatable with respect to said catheter tube, said segment including an irrigation port in fluid communication with said center passage.

3. The ventilating and aspirating apparatus of claim 2 wherein the distal end of said catheter tube is oriented at an angle from said catheter axis.

4. The ventilating and aspirating apparatus of claim 3 wherein said catheter tube has a permanent bend of approximately 20 degrees from said catheter axis disposed approximately one inch from the distal end of said catheter tube.

5. A ventilating and aspirating apparatus according to claim 1 further comprising sealing means including a collapsible envelope, said sealing means being mounted to surround said sheath and the portion of said catheter tube residing between said sheath and said manifold.

6. The ventilating and aspirating apparatus of claim 5 wherein said collapsible envelope includes a first segment extending between the proximal end of said manifold and the distal end of said valve and a second segment extending between the proximal end of said valve and the proximal end of said sheath.

7. The ventilating and aspirating apparatus of claim 5 wherein said manifold includes a segment rotatable with respect to said catheter tube, said segment including an irrigation port in fluid communication with said center passage.

8. The ventilating and aspirating apparatus of claim 7 wherein the distal end of said catheter tube is oriented at an angle from said catheter axis.

9. The ventilating and aspirating apparatus of claim 8 wherein said catheter tube has a permanent bend of approximately 20 degrees from said catheter axis disposed approximately one inch form the distal end of said catheter tube.

10. The ventilating and aspirating apparatus of claim 1, including indicia means associated with said apparatus indicating either or both the radial positioning and the longitudinal advancement of said catheter tube.

11. A ventilating and aspirating apparatus for delivering respiratory gases to the trachea of a patient and aspirating congested lungs and breathing passageways comprising: a flexible catheter tube having a catheter lumen and a longitudinal catheter axis, said catheter tube being extendable into and withdrawable form a patient's trachea and having a distal end structured to permit secretions to enter said catheter lumen;
- a vacuum valve with an inlet connected to the lumen of said catheter tube, an outlet constituting means for connection to a vacuum source, and an actuator for selectively communicating the lumen of said catheter tube with the vacuum source;
- a resilient, pliable sheath having a longitudinal sheath axis, said sheath receiving and coaxially surrounding said catheter tube and having an open distal end through which said catheter tube is slidable and being split along a substantial portion of its length; and
- a manifold connected to the distal end of said sheath and having a center passage in open communication with the interior of said sheath, said manifold including means for establishing a fluid connection between said center passage and a patient ventilation and exhalation apparatus and being structured to permit slidable passage of said catheter tube through said center passage.

12. The ventilating and aspirating apparatus of claim 11 wherein the inlet of said vacuum valve extends into the interior of said sheath through said split and engages the proximal open end of said catheter tube, said valve thereby being slidable along the length of the sheath during extension or withdrawal of the catheter tube.

13. A ventilating and aspirating apparatus for delivering respiratory gases to the trachea of a patient and aspirating congested lungs and breathing passageways, comprising:
- a flexible catheter tube having a catheter lumen and a longitudinal catheter axis, said catheter tube being extendable into and withdrawable from a patient's trachea and having a distal end structured to permit secretions to enter said catheter lumen and further having an open proximal end;
- a vacuum valve with an inlet connected to said open proximal end of said catheter tube, an outlet constituting means for connection to a vacuum source, and an actuator for selectively communicating the lumen of said catheter tube with the vacuum source;
- a manifold having a distal end, a proximal end and a center passage, said manifold including means for establishing a fluid connection between said center passage and a patient ventilation and exhalation apparatus and being structured to permit slidable passage of said catheter tube through said center passage;
- swivel means connected to said manifold including a first swivel structure rotatably mounted to the distal end of said manifold and a second swivel structure rotatably mounted to the proximal end of said manifold, said first and second swivel structures having respective interiors in open communication with said center passage; and
- an "O"-ring disposed within said manifold, said "O"-ring fitting coaxially over said catheter tube thereby isolating the distal portion of said catheter extending beyond said "O"-ring.

14. The ventilating and aspirating apparatus of claim 13 wherein said second swivel structure includes an irrigation port in fluid communication with said center passage.

15. The ventilating and aspirating apparatus of claim 13 wherein the distal end of said catheter tube is oriented at an angle from said catheter axis.

16. The ventilation and aspirating apparatus of claim 13, including a semirigid sheath, said sheath receiving and coaxially surrounding said catheter tube and having an open distal end through which said catheter tube is slidable.

17. A ventilating and aspirating apparatus according to claim 13 further comprising sealing means including a collapsible envelope, said sealing means being mounted to surround the proximal portion of said catheter tube extending from said manifold.

18. The ventilating and aspirating apparatus of claim 17 wherein said collapsible envelope includes a first segment extending between the proximal end of said second swivel structure and the distal end of said valve and a second segment extending between the proximal end of said valve and the proximal end of said sheath.

19. The ventilating and aspirating apparatus of claim 17 wherein said second swivel structure includes an irrigation port in fluid communication with said center passage.

20. The ventilating and aspirating apparatus of claim 17 wherein the distal end of said catheter tube is oriented at an angle from said catheter axis.

21. The ventilation and aspirating apparatus of claim 17, including a semirigid sheath, said sheath receiving and coaxially surrounding said catheter tube and having an open distal end through which said catheter tube is slidable.

22. The ventilating and aspirating apparatus of claim 13, including indicia means associated with said apparatus indicating either or both the radial positioning and the longitudinal advancement of said catheter tube.

23. A ventilating and aspirating apparatus for delivering respiratory gases to the trachea of a patient and aspirating congested lungs and breathing passageways, comprising:
- a flexible catheter tube having a catheter lumen and a longitudinal catheter axis, said catheter tube being extendable into and withdrawable from a patient's trachea and having a distal end structured to permit secretions to enter said catheter lumen and further having an open proximal end;
- a vacuum valve with an inlet connected to said open proximal end of said catheter tube, an outlet constituting means for connection to a vacuum source, and an actuator for selectively communicating the lumen of said catheter tube with the vacuum source, said actuator comprising a resilient cap with a depending valve stem cooperatively associated with a valve body including said inlet and said outlet;

a resilient pliable sheath having a longitudinal sheath axis, said sheath receiving and coaxially surrounding said catheter tube and having an open distal end through which said catheter tube is slidable;

a manifold connected to the distal end of said sheath and having a center passage in open communication with the interior of said sheath, said manifold including means for establishing a fluid connection between said center passage and a patient ventilation and exhalation apparatus and being structured to permit slidable passage of said catheter tube through said center passage; and an "O"-ring disposed within said manifold, said "O"-ring fitting coaxially over said catheter tube thereby isolating the distal portion of said catheter tube extending beyond said "O"-ring.

24. The ventilating and aspirating apparatus of claim 23 wherein said manifold includes a segment rotatable with respect to said catheter tube, said segment including an irrigation port in fluid communication with said center passage.

25. The ventilating and aspirating apparatus of claim 23 wherein said sheath is a thick walled, plastic tube with a split between opposed sidewalls.

26. The ventilating and aspirating apparatus of claim 23 wherein said catheter tube includes a permanent bend disposed near its distal end so that said distal end is inclined from said catheter axis.

27. The ventilating and aspirating apparatus of claim 26 wherein said sheath is split parallel said sheath axis.

28. The ventilating and aspirating apparatus of claim 27 wherein the said vacuum valve is mounted so that its inlet extends into the interior of said sheath through said split and engages the proximal open end of said catheter tube, said inlet thereby being slidable along the length of the sheath to extend or withdraw said catheter tube by moving said valve towards or away from, respectively, the distal end of said sheath.

29. A ventilating and aspirating apparatus according to claim 23, further comprising sealing means including a collapsible envelope, said sealing means being mounted to surround said sheath and the portion of said catheter tube residing within said sheath.

30. The ventilating and aspirating apparatus of claim 29 wherein said collapsible envelope includes a first segment extending between the proximal end of said manifold and the distal end of said valve and a second segment extending between the proximal end of said valve and the proximal end of said sheath.

31. The ventilating and aspirating apparatus of claim 29 wherein said manifold includes a segment rotatable with respect to said catheter tube, said segment including an irrigation port in fluid communication with said center passage.

32. The ventilating and aspirating apparatus of claim 29 wherein said sheath is a thick walled, plastic tube with a split between opposed sidewalls.

33. The ventilating and aspirating apparatus of claim 29 wherein said catheter tube includes a permanent bend disposed near its distal end so that said distal end is inclined from said catheter axis.

34. The ventilating and aspirating apparatus of claim 23, including indicia means associated with said apparatus indicating either or both the radial positioning and the longitudinal advancement of said catheter tube.

35. A ventilating and aspirating apparatus for delivering respiratory gases to the trachea of a patient and aspirating congested lungs and breathing passageways comprising:

a flexible catheter tube having a catheter lumen and a longitudinal catheter axis, said catheter tube being extendable into and withdrawable from a patient's trachea and having a distal end structured to permit secretions to enter said catheter lumen;

a vacuum valve with an inlet connected to the lumen of said catheter tube, an outlet constituting means for connection to a vacuum source, and an actuator for selectively communicating the lumen of said catheter tube with the vacuum source;

a resilient, pliable sheath having a longitudinal sheath axis, said sheath receiving and coaxially surrounding said catheter tube and having an open distal end through which said catheter tube is slidable and being split along a substantial portion of its length;

a manifold connected to the distal end of said sheath and having a center passage in open communication with the interior of said sheath, said manifold including means for establishing a fluid connection between said center passage and a patient ventilation and exhalation apparatus and being structured to permit slidable passage of said catheter tube through said center passage; and sealing means including a collapsible envelope, said sealing means being mounted to surround said sheath and the portion of said catheter tube residing between said sheath and said manifold.

36. The ventilating and aspirating apparatus of claim 35 wherein the inlet of said vacuum valve extends into the interior of said sheath through said split and engages the proximal open end of said catheter tube, said valve thereby being slidable along the length of the sheath during extension or withdrawal of the catheter tube.

37. A ventilating and aspirating apparatus for delivering respiratory gases to the trachea of a patient and aspirating and irrigating congested breathing passageways comprising:

a flexible catheter tube having a catheter lumen and a longitudinal catheter axis, said catheter tube being extendable into and withdrawable from a patient's trachea and having a distal end structured to permit secretions to enter said catheter lumen and further having an open proximal end and a permanent bend disposed near said distal end so that said distal end is inclined from said catheter axis;

a vacuum valve with an inlet connected to said open proximal end of said catheter tube, an outlet constituting means for connection to a vacuum source, and an actuator for selectively communicating the lumen of said catheter tube with the vacuum source, said actuator comprising a resilient cap with a depending valve stem cooperatively associated with a valve body including said inlet and said outlet;

a resilient pliable sheath having a longitudinal sheath axis, said sheath receiving and coaxially surrounding said catheter tube and having an open distal end through which said catheter tube is slidable and being split parallel said sheath axis; and a manifold connected to the distal end of said sheath and having a center passage in open communication with the interior of said sheath, said manifold including means for establishing a fluid connection between said center passage and a patient ventilation and exhalation apparatus and being structured to permit slidable passage of said catheter tube through said center passage.

38. The ventilating and aspirating apparatus of claim 37 wherein the said vacuum valve is mounted so that its inlet extends into the interior of said sheath through said split and engages the proximal open end of said catheter tube, said inlet thereby being slidable along the length of the sheath to extend or withdraw said catheter tube by moving said valve towards or away from, respectively, the distal end of said sheath.

* * * * *